United States Patent [19]

Davidson

[11] Patent Number: 5,105,000

[45] Date of Patent: Apr. 14, 1992

[54] ABSTRACTING ELECTRO-NEGATIVE ELEMENTS FROM HETERO-MOLECULES

[75] Inventor: Iain M. T. Davidson, Leicester, England

[73] Assignee: University of Leicester, Leicester, England

[21] Appl. No.: 521,667

[22] Filed: May 10, 1990

[30] Foreign Application Priority Data

May 12, 1989 [GB] United Kingdom ............... 8910967

[51] Int. Cl.[5] ................................................ C07F 7/08
[52] U.S. Cl. ................................... 556/477; 556/468; 204/157.74
[58] Field of Search .............................. 556/477, 468; 204/157.74

[56] References Cited

U.S. PATENT DOCUMENTS 2,474,087  6/1949  Barry et al. .......................... 556/468
2,511,820  6/1950  Barry et al. ...................... 556/477 X
4,962,219 10/1990  Halm et al. ........................ 556/468

FOREIGN PATENT DOCUMENTS 0028009  5/1981  European Pat. Off. .
0695230 10/1950  United Kingdom ................ 556/468
2144137A  2/1985  United Kingdom .

OTHER PUBLICATIONS

Nagai, Y., "The Chemistry of Organosilicon Free Radicals", *Infra-Science Chemistry Reports*, vol. 4(2), 1970, pp. 115–125.

Oka et al., "Photo-Induced Free Radical Chlorinative Cleavage of Tris(tri-methylsilyl)phenylsilane with Carbon Tetrachloride", *Chem. Express*, vol. 4, 1989, pp. 789–792.

Sakurai, "Group IVB Radicals", *Free Radicals*, vol. 2, 1973, pp. 741–808 (Wiley, New York).

*Primary Examiner*—Paul F. Shaver
*Attorney, Agent, or Firm*—Renner, Otto, Boisselle & Sklar

[57] ABSTRACT

There is disclosed a process for abstracting electro-negative elements from hetero-molecules, comprising reacting said hetero-molecules under anhydrous conditions with reactive organo-silicon intermediates selected from the group consisting of silyl free radicals and silylenes. The process is particularly suitable for the destruction of existing chlorinated fluorocarbons.

14 Claims, No Drawings

ABSTRACTING ELECTRO-NEGATIVE ELEMENTS FROM HETERO-MOLECULES

BACKGROUND TO THE INVENTION

This invention relates to a process for abstracting electronegative elements from hetero-molecules.

Damage to the protective ozone layer in the stratosphere is now of considerable concern. The main threat comes from chlorine radicals, formed by the action of sunlight on chlorinated fluorocarbons of the general formula $C_nF_xCl_yH_z$, (where n, x, y ≧ 1; z ≧ 0)—particularly dichlorodifluoromethane—which are used as aerosol propellants and as the working fluid in refrigerators, freezers and air conditioning equipment.

Although banning wherever possible the future use of chlorinated flurorocarbons (and particularly polychlorinated fluorocarbons; y ≧ 2) may alleviate ozone destruction to an extent, many third world countries, unable to afford advanced technologies free of chlorinated fluorocarbons, plan substantial increases in their consumption.

Provision of environmentally less hostile chlorinated fluorocarbons, which may be used in such countries, as well as a method of destroying existing stocks of chlorinated fluorocarbons, should help to maintain the ozone layer.

The present invention has particular importance in abstracting chlorine from chlorinated fluorocarbons to yield products having a reduced chlorine component. Inter alia, the invention relates to a process for the formation of ecologically benign halocarbons of the kind that might be used even in those countries at present unable to afford CFC-free technologies.

The present invention provides a process for the abstraction of electronegative elements from heteromolecules and is illustrated with reference to the production, from chlorinated fluorocarbons, of relatively ecologically benign halocarbons.

SUMMARY OF THE INVENTION

According to the present invention there is provided a process for abstracting electro-negative elements from hetero-molecules, comprising reacting said hetero-molecules under anhydrous conditions with reactive organo-silicon intermediates selected from the group consisting of silyl free radicals and silylenes.

The process may be operated in the gas phase at low partial pressures.

The hetero-molecules may be characterised by comprising at least one carbon and one halogen atom.

Said hetero-molecules may be selected from the group consisting of chlorinated fluorocarbons of the general formula $C_nF_xCl_yH_z$, (where n, x, y ≧ 1; z ≧ 0).

Said general formula may include $CFCl_3$; $CF_2Cl_2$ and $CF_3Cl$, for example.

The silyl free radicals may have the general formula $.SiR_1R_2R_3$, where $R_1$, $R_2$ and $R_3$ are aliphatic groups, preferably saturated and having carbon—carbon bond angles of less than 129°.

$R_1$ may be $R_2$.

Preferably $R_1$, $R_2$ and $R_3$ are identical and $R_1$ is comprised by a methyl group—hereinafter denoted by Me).

The process may be carried out at temperatures of about 300° C. during the formation of silyl free-radicals in the industrial process for the manufacture of chlorosilanes by reaction of alkyl chlorides with silicon/copper alloy in a fluidized-bed reactor.

Alternatively, and or additionally, the silyl-free radicals may be formed by the pyrolysis of silyl-free-radical precursors in the presence of a suitable alkyl radical precursor.

Said alkyl radical precursor may be, for example, dimethylmercury.

Said silyl free-radical precursors may be selected from the group consisting of silane hydrides, including alkylsilanes possessing a silicon-hydrogen bond.

Said silyl free-radicals may also be formed by photolysis of suitable precursors of silyl free-radicals.

Silyl free-radicals suitable for carrying out the process according to the invention may include short chain alkylsilyl free-radicals, such as the trimethylsilyl free-radical.

The process according to the invention may be carried out by reaction, under anhydrous conditions, of said hetero-molecules with silylenes, having the general formula $:SiR_1R_2$.

As above, $R_1$ and $R_2$ may be aliphatic groups, preferably saturated and having carbon—carbon bond angles of less than 129°.

$R_1$ may be $R_2$.

Preferably $R_1$ is a methyl group.

The process, according to the invention, may be carried out at temperatures of about 300° C. during the formation of silylenes in the industrial process for the manufacture of chlorosilanes by reaction of alkyl chlorides with silicon/copper alloy in a fluidised-bed reactor.

Said silylenes may, however, be formed by the pyrolysis of suitable silylene precursors including those having the general formulae $R_5Si_2X$ and $(XR_2Si)_2$; where R comprises an alkyl group such as a methyl or ethyl group and X is selected from the group consisting of H, OMe and a halogen atom.

Thus said silylene precursors may be selected from the group consisting of methoxydisilanes, halodisilanes and alkyldisilanes which possess at least one silicon—hydrogen bond.

Silylenes suitable for carrying out the invention may include dimethylsilylene.

DETAILED DISCLOSURE OF THE PREFERRED EMBODIMENTS

The invention will be further apparent from the following description, with reference to the several examples which serve only to illustrate the process according to the invention.

The invention comprises a process for abstracting electro-negative elements such as chlorine from hetero-molecules, comprising reacting said hetero-molecules under anhydrous conditions with reactive organo-silicon intermediates selected from the group consisting of silyl free-radicals having the general formula $.SiR_1R_2R_3$, and silylenes having the general formula $:SiR_1R_2$.

The hetero-molecules, which in the Examples are selected from the group consisting of the chlorinated fluorocarbons: $CFCl_3$, $CF_2Cl_2$ and $CF_3Cl$ comprise at least one carbon and one halogen atom.

$R_1$, $R_2$ and $R_3$ attached to the silicon atom comprised by the silyl free-radicals are aliphatic groups and, as illustrated by Example 4, are identical, being comprised by a methyl group.

Likewise in the case of the Examples relating to silylenes, the aliphatic groups attached to the silicon atom comprised thereby are methyl groups.

EXAMPLE 1

$CF_2Cl_2 + Me_2Si$:

Dimethylsilylene ($:SiMe_2$) was generated by pyrolysis of $Me_3SiSiMe_2H$ in the presence of $CF_2Cl_2$ [1:1 mixture, partial pressures 1-2 mmHg] between 711 and 788 K (438°-515° C.). Substantial amounts of $Me_3SiSiMe_2Cl$ were formed, with $CF_2ClH$ and various other products. These products did not include any fluorosilanes or products resulting from insertion of $:SiMe_2$ into $CF_2Cl_2$. The $Me_3SiSiMe_2H$ disappeared significantly faster than when it was pyrolysed alone. These results are consistent with a radical chain sequence initiated by an abstraction reaction by $:SiMe_2$, thus:

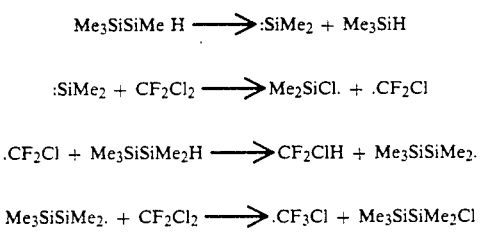

$$Me_3SiSiMe_2H \longrightarrow :SiMe_2 + Me_3SiH \quad (1)$$

$$:SiMe_2 + CF_2Cl_2 \longrightarrow Me_2SiCl\cdot + \cdot CF_2Cl \quad (2)$$

$$\cdot CF_2Cl + Me_3SiSiMe_2H \longrightarrow CF_2ClH + Me_3SiSiMe_2\cdot \quad (3)$$

$$Me_3SiSiMe_2\cdot + CF_2Cl_2 \longrightarrow \cdot CF_3Cl + Me_3SiSiMe_2Cl \quad (4)$$

Approximate relative product formation is given in Table 1 and was calculated from measured gc peak areas for those compounds which were completely separated by gc. $CF_2$ and $CF_2ClH$ were not fully separated on the gc column, and the relative amount of these was estimated from the mass spectrum of the mixture: neither compound gave strong molecule-ion peaks, but $CF_2ClH$ has a prominent peak at m/e 51 ($CF_2^+H$), not present in $CF_2Cl_2$, while both compounds have peaks at m/e 85, 87 ($CF_2Cl^+$).

EXAMPLE 2

$CFCl_3 + Me_2Si$:

A 1:3 mixture of $Me_3SiSiMe_2H$ and $CFCl_3$, partial pressures 0.5-1.5 mmHg, was pyrolysed between 719 and 772 K (446°-499° C.). The course of the reaction was very similar to Example 1 above; $Me_3SiSiMe_2Cl$ was the major product, with $CFCl_2H$, $Me_3SiCl$, and $Me_2SiCl_2$. Me was observed as a very minor product. $Me_3SiCl$ increased relative to the other products with increasing temperature, becoming the major product at the top of the temperature range. [$Me_3SiSiMe_2Cl$ decomposes to form $Me_3SiCl$ in a silylene elimination analogous to reaction scheme 2 in Example 1].

In this case, $CFCl_2H$ and $CFCl_3$ were separated on the gc column, and their relative amounts, shown in Table 1, were estimated directly from gc peak areas.

EXAMPLE 3

$CF_3Cl + Me_2Si$:

A 1:3 mixture of $Me_3SiSiMe_2H$ and $CF_3Cl$, partial pressures 1-2 mmHg, was pyrolysed between 684 and 763 K (411°-490° C.). The major products were $Me_3SiSiMe_2Cl$ and $Me_3SiCl$; separate experiments with authentic samples showed that $CF_3H$ had the same retention time as $CF_3Cl$; the relative amount of these compounds given in Table 1 was therefore deduced from mass spectral peaks [m/e 51 ($CF_2H^+$) and m/e 69 ($CF_3^+$)].

EXAMPLE 4

$CF_2Cl_2 + Me_3Si\cdot$ and $CFCl_1 + Me_3Si\cdot$.

$Me_2Mg$ was pyrolysed in the presence of $Me_3SiH$ to produce methyl radicals which react therewith. Accordingly, a mixture of $CF_2Cl_2$, $Me_3SiH$, and $Me_2Hg$ [10:10:1] was pyrolysed between 693 and 798 K (420°-525° C.). Me (simply resulting from combination of $Me_3Si$. radicals) was the major product, and $Me_3SiCl$ a minor product.

The proportion of $Me_2Hg$ in the mixture was doubled, and the temperature range extended to 769-857 K (496°-584° C.). Under these conditions most of the $Me_3SiH$ disappeared, substantial quantities of $Me_3SiCl$ were produced (implying $Me_3Si$. radical attack on $CF_2Cl_2$ as expected), but no $CF_2ClH$ was detected. The only fluorine-containing product observed was $Me_3SiF$; [$Me_3SiF$]/[$Me_3SiCl$] ranged from ca. 0.048 at 519° C. to ca 0.18 at 577° C.

Similar experiments with this higher proportion of $Me_2Hg$ using $CFCl_3$ instead of $CF_2Cl_2$ between 714 and 871 K (441°-598° C.) also gave $Me_3SiCl$ and $Me_3SiF$ as the main products, again with substantial loss of $Me_3SiH$, but [$Me_3SiF$]/[$Me_3SiCl$] was greater than in the experiments with $CF_2Cl$hd 2, ca. 0.24 at 598° C.

TABLE 1

Relative Product Formation in Reactions of Dimethysilylene with Chlorinated Flurocarbons

| T/°C. | [CDS]/[CFC] | [CDS]/[CFH] | [CFH]/[CFC] |
|---|---|---|---|
| $CF_2Cl_2$ | | | |
| 442 | 4.5 | 3.1 | 1.5 |
| 462 | 3.6 | 1.7 | 2.1 |
| 480 | 3.0 | 1.8 | 1.7 |
| $CFCl_3$ | | | |
| 446 | 0.76 | 4.1 | 0.19 |
| 473 | 0.56 | 3.0 | 0.19 |
| 499 | 1.8 | 1.8 | 0.96 |
| $CF_3Cl$ | | | |
| 448 | 0.38 | 9.4 | 0.04 |
| 486 | 0.45 | 6.0 | 0.08 |

PRODUCT FORMATION IN REACTIONS OF CHLORINATED FLUOROCARBONS WITH DIMETHYLSILYLENE

Relative product formation in these reactions is given in Table 1. It should be emphasized that the FIGS. in the table do not relate to the relative proportion of products at completion of the various reactions, being simply an indication of the products at an initial stage in the reaction, CFC an dCFH denote the chlorofluorocarbon and corresponding hydride respectively, i.e. $CF_2Cl_2$ and $CF_2ClH$, $CFCl_3$ and $CFCl_2H$, and $CF_3Cl$ and $CF_3H$. CDS denotes the chlorodisilane, $Me_3SiSiMe_2Cl$.

The [CDS]/[CFC]and [CFF]/[CFC]columns in the Table are measures of the extent of reaction: under the conditions chosen, the extent of reaction was greatest for $CF_2Cl_2$ and least for $CF_3Cl$. In all three cases, the [CDS]/[CFH] ratio decreased with increasing temperature, implying that the activation energy for formation of CFH is greater than the activation energy for the formation of CDS. From the data in the [CDS]/[CFH]column, this activation energy difference was ca. 65 kJmol$^{-1}$ for $CF_2Cl_2$, 69 kJmol$^{-1}$ for $CFCl_3$, and 54 kJmol$^{-1}$ for $CF_3Cl$.

REACTIONS OF CHLORINATED FLUOROCARBONS WITH TRIMETHYLSILYL FREE RADICALS

The formation of $Me_3SiCl$ as a major product is in accordance with the abstraction of chlorine from chlorinated fluorocarbons by free radical attack thereon.

Large quantities of $Me_3Si\cdot$ radicals were produced, as evidenced by the substantial loss of $Me_3SiH$ and by the formation of $Me_6Si_2$ as the main product as described in Example 4. This swamping of the system with $Me_3Si\cdot$ radicals probably accounts for the formation of some $Me_3SiF$; no $Me_3SiSiMe_2F$ was observed along with the $Me_3SiSiMe_2Cl$ in the experiments with $Me_2Si\!:$. Carbon-centred radicals formed from the chlorinated fluorocarbons were probably scavenged by the large quantities of $Me_3Si\cdot$ and $Me\cdot$ radicals present, thus inhibiting radical abstractions analogous to reaction (3) in Example 1, and preventing the formation of CFH species.

It will be appreciated that it is not intended to limit the invention to the above examples only, many variations, such as might readily occur to one skilled in the art, being possible, without departing from the scope thereof as defined by the appended claims.

For example, although pyrolysis at temperatures in the region of 400° to 500° C. of silylene and silyl free-radical precursors in the presence of chlorinated fluorocarbons has been particularly described, the process according to the invention may be carried out at temperatures of about 300° C. during the formation of silyl free radicals or silylenes in the industrial process for the manufacture of chlorosilanes by reaction of alkyl chlorides with silicon/copper alloy in a fluidised-bed reactor.

It is to be stressed that the temperature described in the Examples are those under which the reactive organo-silicon intermediates have been produced, and considerably lower temperatures may be involved in abstraction of electronegative elements from heteromolecules where said intermediates are produced by less energetic means.

Thus the silyl free-radicals and silylenes may be formed by photolysis of suitable precursors of silyl-free radicals and silylenes in the temperature range from 0° C. up to those temperatures described in the examples.

Although it is preferred that the groups comprised by $R_1$, $R_2$ and $R_3$ are low molecular weight saturated alkyl groups having carbon—carbon bond angles of less than 129°, larger unsaturated such groups may be used in the method according to the invention although such groups may undergo intra-molecular rearrangement during reaction with the heteromolecules which could reduce the efficiency of reaction perhaps by generating a competitive reaction pathway.

The silyl free radicals and silylenes are not limited to those described in the Examples many further variations thereof for use in the method according to the invention being possible For example, such further variations include $(CH_3)_2C_2H_5Si\cdot$ and $(CH_3)_2Si\!:$.

The abstraction of chlorine from polychlorinated fluorocarbons, according to the invention, may be adapted for the on-line production of relatively ecologically benign chlorinated fluorocarbons as the said polychlorinated fluorocarbons are produced. Preferably the process involves separation of the polychlorinated fluorocarbons from their precursors during synthesis thereof, so that abstraction of chlorine from said polychlorinated fluorocarbons to produce relatively ecologically benign chlorinated fluorocarbons in the manner according to the invention does not alter the equilibria between said precursors and said polychlorinated fluorocarbons.

The process according to the invention is adaptable for the on-line production of relatively ecologically benign chlorinated fluorocarbons from polychlorinated fluorocarbons which are produced as by-products of other processes.

The process, of course, is particularly suitable for the destruction of existing chlorinated fluorocarbons.

I claim:

1. A process for abstracting halogen atoms from halogen-containing molecules, comprising reacting said halogen-containing molecules under anhydrous conditions with reactive organo-silicon intermediates selected from the group consisting of silylene.

2. A process according to claim 1, characterized in that it is carried out in the gas phase at low partial pressure.

3. A process according to claim 1, characterized in that said halogen-containing molecules have the general formula $C_nF_xCl_yH_z$, where n, x, $y \geq 1$; $z \geq 0$.

4. A process according to claim 3, characterized in that said general formula includes $CFCl_3$; $CF_2CL_2$ and $CF_3Sl$.

5. A process according to claim 1, characterised in that said silylenes have the general formula $:SiR_1R_2$.

6. A process according to claim 5, characterised in that $R_1$ and $R_2$ are aliphatic groups.

7. A process according to claim 5, characterised in that $R_1 = R_2$.

8. A process according to claim 7, characterised in that $R_1$ is a methyl group.

9. A process according to claim 5, characterised in that said process is carried out at temperatures of about 300° C. during the formation of silylenes in the industrial process for the manufacture of chlorosilanes by reaction of alkyl chlorides with silicon/copper alloy in a fluidised-bed reactor 10. A process according to claim 1, characterised in that said silylenes are formed by the pyrolysis of suitable silylene precursors.

11. A process according to claim 10, characterised in that said silylene precursors include those having the general formulae $R_5Si_2X$ and $(XR_2Si)_2$; where R comprises an alkyl group such as a methyl or ethyl group and X is selected from the group consisting of H, OMe and a halogen atom 12. A process according to claim 11, characterised in that said precursors are selected from the group consisting of halodisilanes, methoxydisilanes and alkyldisilanes.

13. A process according to claim 12, characterised in that an alkyldisilane is pentamethyldisilane.

14. A process according to claim 1, characterized in that said silylenes are selected from the group consisting of dimethylsilylene, diethylsilylene and methylethylsilylene.

* * * * *